(12) United States Patent
Klein et al.

(10) Patent No.: US 11,490,978 B2
(45) Date of Patent: Nov. 8, 2022

(54) INSTRUMENTS WITH ELECTRICALLY ISOLATED COMPONENTS, RELATED SYSTEMS AND METHODS

(71) Applicant: INTUITIVE SURGICAL OPERATIONS, INC., Sunnyvale, CA (US)

(72) Inventors: Jordan M. Klein, Palo Alto, CA (US); William J. Park, San Jose, CA (US); Thomas G. Cooper, Menlo Park, CA (US); Thad Lieb, Santa Barbara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 862 days.

(21) Appl. No.: 16/317,268

(22) PCT Filed: May 19, 2017

(86) PCT No.: PCT/US2017/033529
§ 371 (c)(1),
(2) Date: Jan. 11, 2019

(87) PCT Pub. No.: WO2018/013217
PCT Pub. Date: Jan. 18, 2018

(65) Prior Publication Data
US 2019/0298466 A1 Oct. 3, 2019

Related U.S. Application Data

(60) Provisional application No. 62/362,336, filed on Jul. 14, 2016.

(51) Int. Cl.
*A61B 34/35* (2016.01)
*A61B 34/00* (2016.01)
(Continued)

(52) U.S. Cl.
CPC .......... *A61B 34/70* (2016.02); *A61B 18/1445* (2013.01); *A61B 34/35* (2016.02);
(Continued)

(58) Field of Classification Search
CPC ..... A61B 34/70; A61B 34/35; A61B 18/1445; A61B 2017/00526; A61B 2017/0092; A61B 2017/00929; A61B 2034/305
See application file for complete search history.

(56) References Cited

U.S. PATENT DOCUMENTS 5,569,243 A * 10/1996 Kortenbach ........... A61B 17/29
606/46
8,852,208 B2 10/2014 Gomez et al.
(Continued)

FOREIGN PATENT DOCUMENTS

CN 102188230 B 3/2013
WO WO-2015094493 A1 6/2015

OTHER PUBLICATIONS

International Search Report and Written Opinion for Application No. PCT/US2017/033529, dated Aug. 31, 2017, 11 pages.
(Continued)

*Primary Examiner* — Michael F Peffley
*Assistant Examiner* — Bo Ouyang
(74) *Attorney, Agent, or Firm* — Jones Robb, PLLC

(57) ABSTRACT

A surgical instrument component for coupling an end effector to a shaft of a surgical instrument may comprise a distal portion made of an electrically conductive first material, a proximal portion made of an electrically conductive second material, and an intermediate portion made of an electrically insulating third material. The intermediate portion is disposed between and integrally connected to the proximal portion and to the distal portion.

22 Claims, 5 Drawing Sheets

(51) Int. Cl.
  *A61B 18/14* (2006.01)
  *A61B 34/30* (2016.01)
  *A61B 17/00* (2006.01)

(52) U.S. Cl.
  CPC .......... *A61B 2017/0092* (2013.01); *A61B 2017/00526* (2013.01); *A61B 2017/00929* (2013.01); *A61B 2034/305* (2016.02)

(56) References Cited

U.S. PATENT DOCUMENTS

| | | | |
|---|---|---|---|
| 9,089,351 B2 | 7/2015 | Park et al. | |
| 2004/0267254 A1* | 12/2004 | Manzo | A61B 34/37 606/39 |
| 2010/0016853 A1* | 1/2010 | Burbank | A61B 34/71 606/48 |
| 2011/0288573 A1* | 11/2011 | Yates | A61B 17/07207 606/170 |
| 2012/0215220 A1 | 8/2012 | Manzo et al. | |
| 2013/0197484 A1* | 8/2013 | Seddon | A61B 1/00071 604/533 |
| 2013/0325031 A1 | 12/2013 | Schena et al. | |
| 2013/0325033 A1 | 12/2013 | Schena et al. | |
| 2014/0012290 A1 | 1/2014 | Cooper et al. | |
| 2014/0128886 A1 | 5/2014 | Holop et al. | |
| 2014/0227106 A1 | 8/2014 | Jackson et al. | |
| 2019/0021805 A1 | 1/2019 | Roeder et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

INSTRUMENTS WITH ELECTRICALLY ISOLATED COMPONENTS, RELATED SYSTEMS AND METHODS

CROSS-REFERENCE TO RELATED APPLICATIONS

This application is a U.S. national stage application under 35 U.S.C. § 371(c) of International Application No. PCT/US2017/033529, filed on May 19, 2017, which claims priority to U.S. Provisional Application 62/362,336, filed Jul. 14, 2016, each of which is incorporated by reference herein in their entirety.

Aspects of the present disclosure relate to instruments including electrically isolated portions or components.

INTRODUCTION

Various medical instruments or tools (including surgical instruments or tools) can be configured to apply electrical energy (e.g., electrosurgical energy) to an operating site to carry out a medical procedure (including surgical procedures). For example, a surgical instrument may be configured to seal, bond, ablate, fulgurate, etc. tissue through the application of an electrical current. In some cases, the body of a patient is held at a ground (e.g., zero) electrical potential, while a portion of the surgical instrument is brought to a different electrical potential (e.g., by an operator command to the instrument of through a surgeon console in the case of a teleoperated surgical system) to deliver electrical energy to the surgical site.

In some circumstances, other energized or non-energized medical instruments (e.g. surgical instruments) are in use at the operation site (e.g. surgical site) in the proximity of the electrosurgical instrument. Such instruments typically include components comprising electrically conductive materials, such as metals and metal alloys. If an electrically energized instrument is close to or touching a conductive, non-energy delivering instrument, the electrical energy may flow into the non-energy delivering instrument. The electrical energy may be thereby misdirected from the intended application site.

Providing electrical insulation for such tools may be difficult for various reasons. For example, for surgery applications, surgical instruments such as clamps, forceps, grippers, shears, etc. are often configured to deliver relatively high magnitudes of force to carry out desired surgical operations. To withstand such forces and provide durability, such surgical instruments may be constructed from metals or metal alloys such as stainless steel, titanium alloys, aluminum alloys, etc., based on material properties such as yield strength, toughness, hardness, or other material properties. Such material, however, are typically relatively highly electrically conductive. Materials with electrical insulating properties, such as, e.g., polymers (e.g., plastics) and ceramics, may not have the desired combination of material properties such as yield strength, toughness, hardness, wear resistance, etc. to use them for components of the surgical instrument that are used for high force application.

A need exists to provide electrically isolated medical instruments that are durable and reliable for use during medical procedures such as surgical procedures, and also for other, non-medical operations where electrically isolated instruments are used.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument component for coupling an end effector to a shaft of a surgical instrument comprises a distal portion made of an electrically conductive first material, a proximal portion made of an electrically conductive second material, and an intermediate portion made of an electrically insulating third material. The intermediate portion is disposed between and integrally connected to the proximal portion and to the distal portion.

In accordance with at least one exemplary embodiment, a surgical instrument comprises a shaft, a clevis attached to a distal end of the shaft, and an end effector coupled to the clevis. The clevis comprises a distal portion made of an electrically conductive first material, a proximal portion made of an electrically conductive second material, and an intermediate portion made of an electrically insulating third material, the intermediate portion being disposed between and integrally connected to the proximal portion and to the distal portion.

In accordance with at least one exemplary embodiment, a method of forming a component for coupling a surgical instrument end effector to a surgical instrument shaft comprises arranging a first electrically conductive part distally and spaced from a second electrically conductive part, and processing an electrically insulating material in the space to integrally connect the electrically insulating material to the first part and to the second part. After the integral connection, the first part is a distal portion of the component, the second part is a proximal portion of the component, and the electrically insulating material is an intermediate portion of the component.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1A:
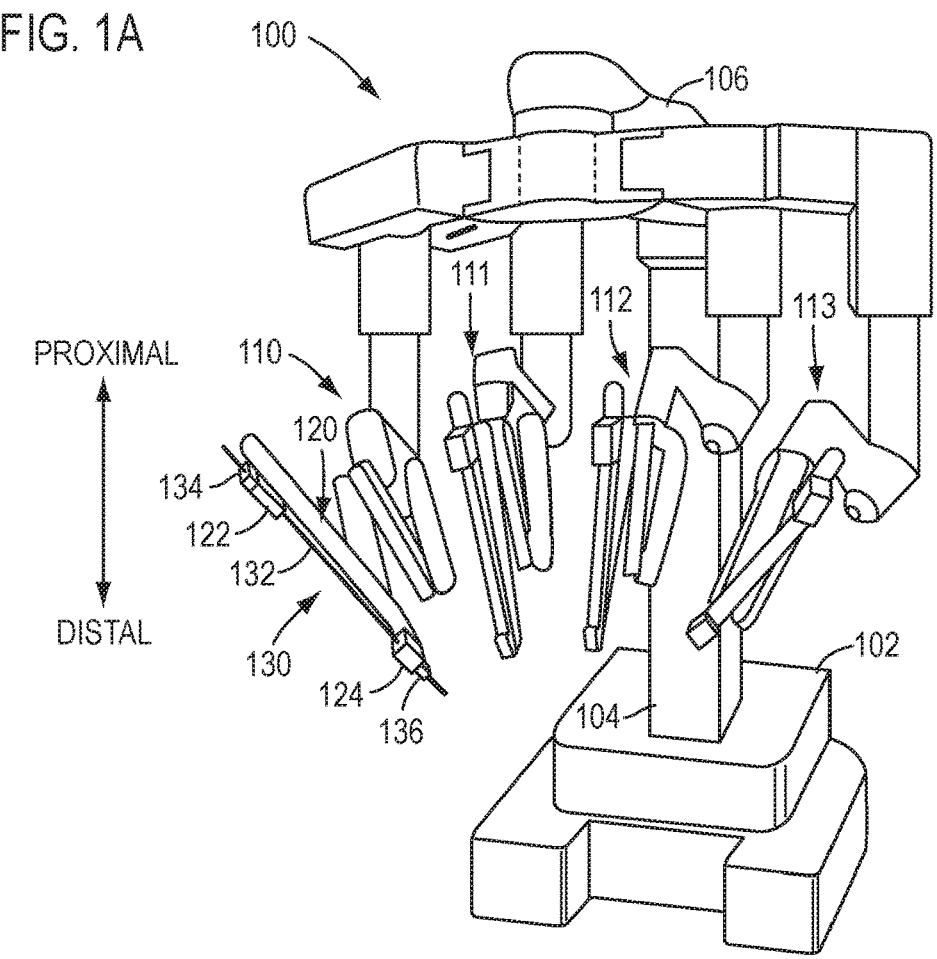
FIG. 1A is a front view of an exemplary embodiment of a patient side cart of a teleoperated surgical system.

The present disclosure contemplates various exemplary embodiments of surgical instruments, medical instruments, non-medical instruments, and related devices that provide for electrical isolation between portions of a component of the instrument. For example, according to some exemplary embodiments of the disclosure, a, medical instrument may include a component with a distal portion and a proximal portion, the distal portion and the proximal portion being electrically isolated from one another. In an exemplary embodiment, the distal portion and the proximal portion comprise electrically conductive materials, such as, for example, metals or metal alloys. An intermediate portion disposed between the distal portion and the proximal portion comprises an electrically insulating material, such as, for example, polymers (e.g., plastics), ceramics, composite materials, etc. Each of the distal portion and the proximal portion comprise one or more engagement features configured to interlock with the intermediate portion. The engagement features may be further configured to be complementary to one another. In other words, one or more engagement features of the distal portion are configured to be complementary to one or more engagement features of the proximal portion. For example, the one or more engagement features of the distal portion may be configured to interact with the one or more engagement features of the proximal portion such that when a bending load or torque load is applied to the distal portion of the clevis, at least a portion of the intermediate portion is placed under compressive force. In exemplary embodiments, the engagement features may include, without limitation, protrusions, recesses, castellations (e.g., teeth or toothed structures), splines, and other features. The engagement features may be configured to be complementary to one another without being in contact with one another.

The engagement features of the distal portion and the proximal portion impart robust structure to the component. For example, the interfaces between the distal portion and the intermediate portion, and the proximal portion and the intermediate portion, (e.g., the engagement features and complementary engagement features) provide a robust mechanical coupling that may exceed the strength that would be provided by, e.g., planar or other shaped interfaces between the portions. Exemplary embodiments of the present disclosure thereby provide medical instruments (such as surgical instruments) with electrical insulation (e.g., isolation) between portions of the instruments while exhibiting sufficient strength and durability to perform desired procedures such as surgical procedures. For example, in exemplary embodiments, a portion of a surgical instrument may exhibit the electrically insulating properties of a material such as a polymer, while other portions of the surgical instrument may exhibit the wear resistance, yield strength, and weldability of a metal material.

Exemplary embodiments described herein may be used, for example, with bedside and teleoperated computer-assisted medical systems. Examples of teleoperated, computer-assisted surgical systems (sometimes referred to as robotic surgical systems) that can be used with exemplary embodiments described herein include those described in, for example, U.S. Patent App. Pub. No. US 2013/0325033 A1, entitled "Multi-Port Surgical Robotic System Architecture" and published on Dec. 5, 2013, U.S. Patent App. Pub. No. US 2013/0325031 A1, entitled "Redundant Axis and Degree of Freedom for Hardware-Constrained Remote Center Robotic Manipulator" and published on Dec. 5, 2013, and U.S. Pat. No. 8,852,208, entitled "Surgical System Instrument Mounting" and published on Oct. 7, 2014, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of components described herein can optionally be used in conjunction with hand-held, manual surgical instruments, other medical instruments, and non-medical instruments.

As discussed above, in accordance with various exemplary embodiments, surgical instruments of the present disclosure are configured for use in teleoperated, computer-assisted surgical systems (sometimes referred to as robotic surgical systems). Referring now to FIG. 1A, an exemplary embodiment of a patient side cart 100 of a teleoperated, computer-assisted surgical system, to which surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware Constrained Remote Center Robotic Manipulator" and published on Dec. 5, 2013, each of which is hereby incorporated by reference in its entirety. Non-limiting, exemplary embodiments of teleoperated surgical systems with which the principles of the present disclosure may be utilized include the da Vinci® Si (model no. IS3000) da Vinci® Si Surgical System, Single Site da Vinci® Surgical System, or a da Vinci® Xi Surgical System, available from Intuitive Surgical, Inc. of Sunnyvale, Calif. However, persons having ordinary skill in the art will appreciate that the present disclosure can be applied to a variety of surgical systems including automated or manual (hand-held) laparoscopic surgical systems, or with other surgical applications.

As shown in the exemplary embodiment of FIG. 1A, patient side cart 100 includes a base 102, a main column 104, and a main boom 106 connected to main column 104. Patient side cart 100 also includes a plurality of arms 110, 111, 112, 113, which are each connected to main boom 106. Arms 110, 111, 112, 113 each include an instrument mount portion 120 to which an instrument 130 may be mounted, which is illustrated as being attached to arm 110. Portions of arms 110, 111, 112, 113 may be manipulated during a surgical procedure according to commands provided by a user at the surgeon console. In an exemplary embodiment, signal(s) or input(s) transmitted from a surgeon console are transmitted to the control/vision cart, which may interpret the input(s) and generate command(s) or output(s) to be transmitted to the patient side cart 100 to cause manipulation of an instrument 130 (only one such instrument being mounted in FIG. 1A) and/or portions of arm 110 to which the instrument 10 is coupled at the patient side cart 100.

Instrument mount portion 120 comprises an actuation interface assembly 122 and a cannula mount 124, with a force transmission mechanism 134 of the instrument 130 connecting with the actuation interface assembly 122, according to an exemplary embodiment. Cannula mount 124 is configured to hold a cannula 136 through which a shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate the instrument 130, as those skilled in the art are familiar with.

Although the exemplary embodiment of FIG. 1A shows an instrument 10 attached to only arm 110 for ease of viewing, an instrument may be attached to any and each of arms 110, 111, 112, 113. An instrument 10 may be a surgical instrument with an end effector as discussed herein. A surgical instrument with an end effector may be attached to and used with any of arms 110, 111, 112, 113. However, the embodiments described herein are not limited to the exemplary embodiment of FIG. 1A and various other teleoperated, computer-assisted surgical system configurations may be used with the exemplary embodiments described herein.

Figure 1B:
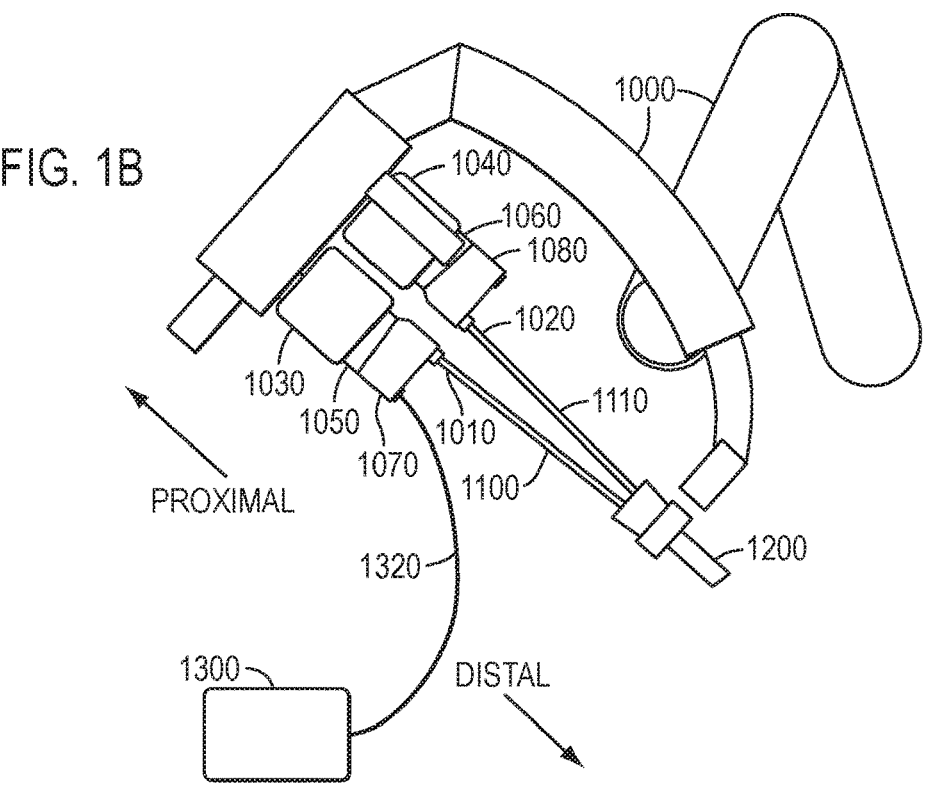
FIG. 1B is a partial schematic view of an exemplary embodiment of a manipulator arm of a patient side cart with two electrosurgical instruments in an installed position, one of which is shown in electrical communication with a flux generator.

Other configurations of surgical systems, such as surgical systems configured for single-port surgery, are also contemplated. For example, with reference now to FIG. 1B, a portion of an exemplary embodiment of a manipulator arm 1000 of a patient side cart with two surgical instruments 1010, 1020 in an installed position is shown. A teleoperated robotic surgical system, including a patient side cart comprising manipulator arm 1000, may be configured according to the exemplary embodiments described in U.S. patent application Ser. No. 14/070,184, filed Nov. 1, 2013 (for "FLUX DISAMBIGUATION FOR TELEOPERATED SURGICAL SYSTEMS"), which is incorporated by reference herein. The schematic illustration of FIG. 1B depicts only two surgical instruments for simplicity, but more than two surgical instruments may be received in an installed position at a patient side cart as those having ordinary skill in the art are familiar with. Each surgical instrument 1010, 1020 includes an instrument shaft 1100, 1110 that at a distal end has a moveable end effector (discussed below in regard to FIG. 2) or a camera or other sensing device, and may or may not include a wrist mechanism (not shown) to control the movement of the distal end.

In the exemplary embodiment of FIG. 1B, the distal end portions of the surgical instruments 1010, 1020 are received through a single port structure 1200 to be introduced into the patient. Other configurations of patient side carts that can be used in conjunction with the present disclosure can use several individual manipulator arms. In addition, individual manipulator arms may include a single instrument or a plurality of instruments. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 1070, 1080 are disposed at a proximal end of each shaft 1100, 1110 and connect through a sterile adaptor 1050, 1060 with actuation interface assemblies 1030, 1040. Actuation interface assemblies 1030, 1040 contain a variety of internal mechanisms (not shown) that are controlled by a controller (e.g., at a control cart of a surgical system) to respond to input commands at a surgeon side console of a surgical system to transmit forces to the force transmission mechanisms 1070, 1080 to actuate instruments 1010, 1020. The diameter or diameters of an instrument shaft, wrist mechanism, and end effector are generally selected according to the size of the cannula with which the instrument will be used and depending on the surgical procedures being performed. In various exemplary embodiments, a shaft and/or wrist mechanism has a diameter of about 4 mm, 5 mm, or 8 mm in diameter, for example, to match the sizes of some existing cannula systems. According to an exemplary embodiment, one or more of surgical instruments 1010, 1020 may be in communication with a flux source 1300 via a flux transmission conduit 1320. For example, if a surgical instrument 1010 is an electrosurgical instrument, flux transmission conduit 1320 is an electrical energy transmission cable and flux source 1300 is an electrical energy generator.

Figure 2:
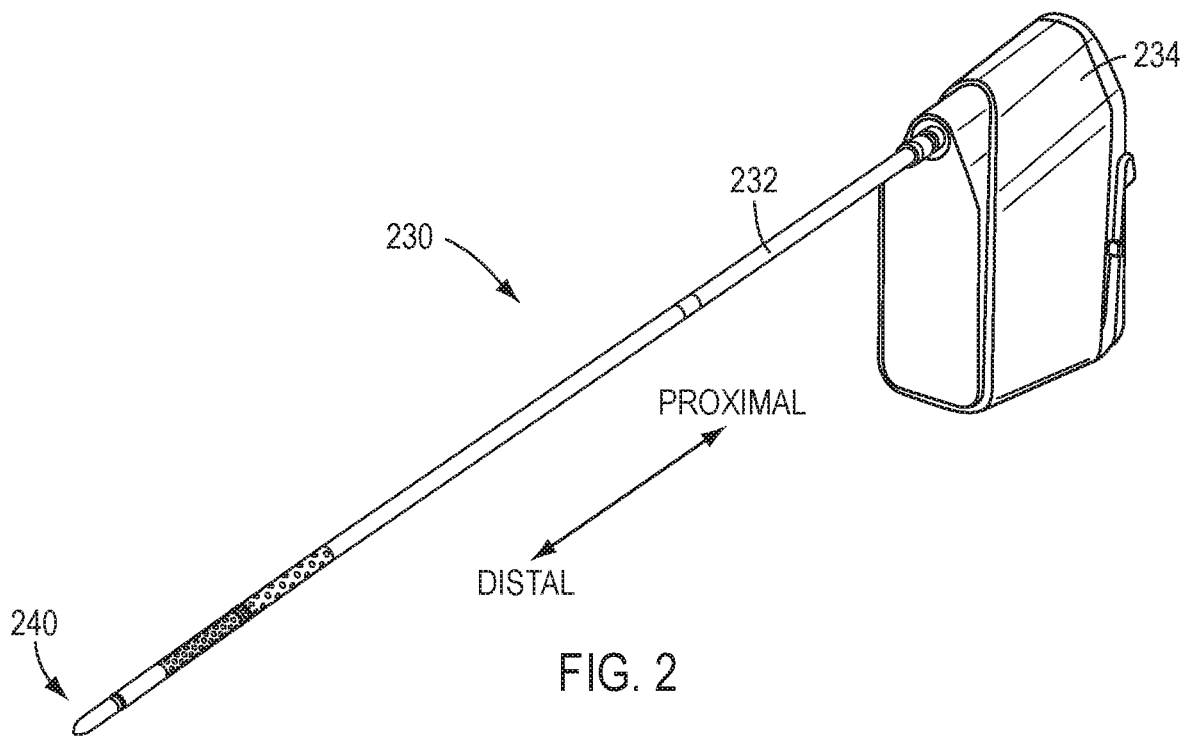
FIG. 2 is a perspective view of an exemplary embodiment of a surgical instrument.

Referring now to FIG. 2, a surgical instrument 230 according to an embodiment of the disclosure is shown. The surgical instrument 230 includes a shaft 232 with an end effector 240 positioned at a distal end thereof. The surgical instrument also includes a force transmission mechanism 234 coupled with a proximal end of the shaft 232 and configured to be operably coupled with an actuation interface assembly (e.g., actuation interface assembly 122 in FIG. 1A).

Figure 3:
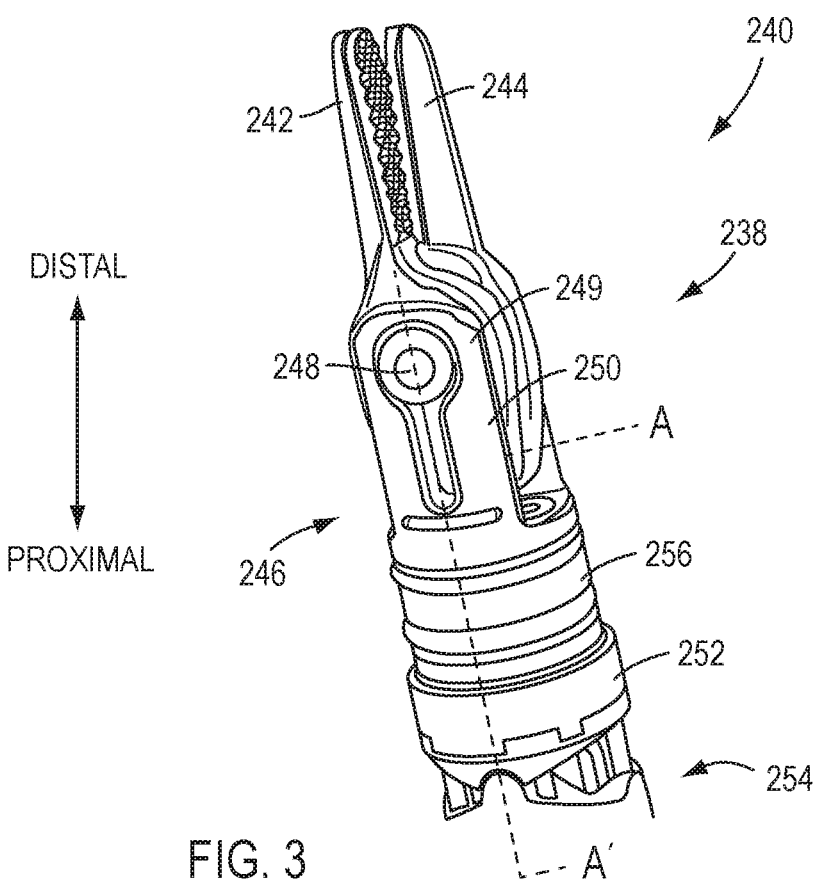
FIG. 3 is a detailed perspective view of a distal end portion of an exemplary embodiment of a surgical instrument including an end effector.

Referring to FIG. 3, a distal end portion 238 of surgical instrument 230 (FIG. 2) is shown including the end effector 240. In an exemplary embodiment, the end effector 240 includes jaws 242 and 244 configured to perform, e.g., a gripping function. The end effector 240 may be or include such surgical tools as forceps, a grasper, a needle driver, a scalpel, scissors, a stapler, a clamp, a cauterizing tool, etc. and need not have a jawed configuration. In the exemplary embodiment of FIG. 3, the end effector 240 is coupled by a clevis 246 to a distal end of the instrument shaft 232 (FIG. 2) or a wrist mechanism 254 (also called "wrist 254") (a portion of which is shown in FIG. 3).

In the exemplary embodiment of FIG. 3, the clevis 246 includes a distal portion 250 including a pivot pin 248 and radially opposing, distally extending prongs 249 configured to provide a slot there between that accepts a portion of end effector 240. The clevis 246 further includes a proximal portion 252 configured for attachment to a portion of the instrument 230 (FIG. 2), such as a wrist 254 configured to impart one or more degrees of freedom of movement to the end effector 240. Other exemplary embodiments may not include a wrist or other joint structure, and the clevis 246 may be coupled directly with the shaft 232 (FIG. 2). In the exemplary embodiment of FIG. 3, the proximal portion 252 of the clevis 246 is attached to a distal portion of the wrist 254 by, e.g., welding. In the embodiment of FIG. 3, the distal portion 250 and the proximal portion 252 of the clevis 246 comprise a relatively highly electrically conductive material, such as, e.g., a metal or metal alloy (such as a titanium alloy, stainless steel, etc.). The material of the distal portion 250 and proximal portion 252 of the clevis 246 may be chosen for material characteristics that include, but are not limited to, hardness (i.e., wear/abrasion resistance), yield strength, machinability, weldability, manufacturing cost, cost of raw materials, etc. As a non-limiting example, the distal portion 250 and the proximal portion 252 may be made from a material exhibiting a yield strength of, as a non-limiting example, between about 1000 MPa (145,000 pounds per square inch) and 2500 MPa (362,600 pounds per square inch). Materials having yield strengths of greater than 2500 MPa, or less than 1000 MPa, are within the scope of the disclosure. In some exemplary embodiments, the material of the distal portion 250 may differ from the material of the proximal portion 252 of the clevis 246. For example, the distal portion 250 and the proximal portion 252 may comprise a single electrically conductive material, e.g., a single metal or metal alloy, or may comprise different electrically conductive materials, e.g., different metals or metal alloys. Forming the proximal portion 252 from a metal or metal alloy may facilitate welding the proximal portion 252 to the distal portion of the wrist 254, or to a distal portion of the shaft 232 in embodiments that do not include the wrist 254. In other exemplary embodiments, one or both of the distal portion 250 and the proximal portion 252 may comprise a non-metal material, such as carbon fiber reinforced plastic, the embedded carbon fibers of which may be electrically conductive. Thus, in exemplary embodiments including such carbon-fiber reinforced plastics in one or both of the distal portion 250 and the proximal portion 252, as with embodiments in which one or both of the distal portion 250 and the proximal portion 252 are made from a metal or metal alloy, electrical insulation between the distal portion 250 and the proximal portion 252 according to exemplary embodiments of the disclosure may be necessary to prevent conduction of electrical current between the distal portion 250 and proximal portion 252.

An intermediate portion 256 of the clevis 246 is disposed intermediate the distal portion 250 and the proximal portion 252. In an exemplary embodiment, the intermediate portion 256 is electrically insulating and comprises a material that is relatively highly electrically insulating (e.g., has a relatively low electrical conductivity) compared to the material(s) of the distal portion 250 and the proximal portion 252 of the clevis 246. For example, the intermediate portion 256 may be made of a polymer material. In an exemplary embodiment, the intermediate portion 256 may comprise a polyphthalamide material, such as, for example, AMODEL® PPA available from Solvay Chemicals. The material of the intermediate portion 256 may be chosen based on material characteristics such as electrical resistivity, arc track resistance, compressive strength, manufacturing cost, cost of raw materials, etc. Additionally, the material of the intermediate portion 256 may be chosen based on suitability for use in injection molding processes. For example, a polymer with high-flow characteristics (e.g., relatively less viscous at a particular temperature) may flow more completely into the space between the distal portion 250 and the proximal portion 252 and prevent occurrence of gaps or other voids in the material of the intermediate portion 256. Polymers capable of being molded at relatively lower temperatures may facilitate injection molding of the intermediate portion 256, as manual handling of the distal portion 250 and proximal portion 252 may be required to place the distal portion 250 and proximal portion 252 within a mold. Lower processing temperatures may mitigate (e.g., reduce) burn danger to which mold operators are exposed during loading and unloading of the mold. For example, in an exemplary embodiment, the material of the intermediate portion may exhibit a melting temperature of between about 100 degrees Celsius and about 200 degrees Celsius, although materials with melting temperatures below 100 degrees Celsius and above 200 degrees Celsius are within the scope of the disclosure. In some exemplary embodiments, the melting temperature of the material may be sufficiently high to enable the material to withstand autoclave temperatures. For example, the melting temperature of the material may be greater than 137 degrees Celsius. In other embodiments, such as in an embodiment configured for a single use thereby eliminating the need to sterilize the component, materials with melting temperatures lower than autoclaving temperatures may be used.

In an exemplary embodiment, the intermediate portion 256 may be made from a material that exhibits a dielectric strength of at least about 100 volts per thousandth of an inch (V/mil), at least about 500 V/mil, at least about 1000 V/mil, or over 1000 V/mil, such as about 4000 V/mil or greater. Further, the dielectric strength of the material of the intermediate portion 256 may be substantially constant across a range of frequencies of an electrical current. For example, the material may exhibit a dielectric strength in the ranges noted above for frequencies of the electrical current of about 1 hertz or more, about 1,000 hertz (1 kHz) or more, about 1,000,000 hertz (1 MHz) or more, or lesser or greater frequencies.

Figure 4:
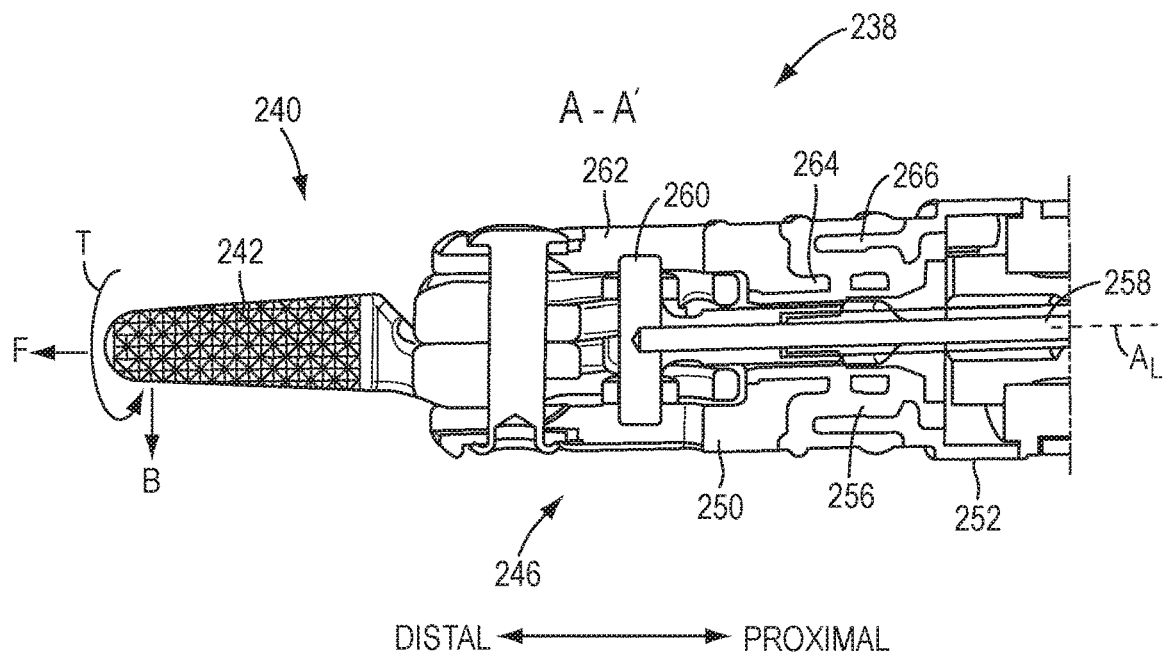
FIG. 4 is a partial, longitudinal cross-sectional view of the distal end portion of the surgical instrument of FIG. 2.

Referring now to FIG. 4, the distal end portion 238 of the instrument (e.g., instrument 230 (FIG. 2) is shown in longitudinal cross-section through section 3-3 in FIG. 2. As shown in FIG. 4, the jaws 242, 244 (only jaw 242 shown in FIG. 4 due to cross-section) of the end effector 240 are actuated by an actuation member 258 passing through a central passage of the instrument 230. The actuation member 258 may be a push/pull member including a head 260, ends of which are positioned in slots 262 formed in the distal portion 250 of the clevis 246. Proximal and distal movement of the actuation member 258 results in actuation (e.g., opening, closing) of the end effector jaws 242, 244 (FIG. 3) as the jaws 242, 244 pivot about pivot pin 248. Movement of the head 260 through the slots 262 of the clevis 246 and resulting actuation of the end effector 240 generates reaction forces and associated stress in the head 260 and slots 262 of the clevis 246. Therefore, reliability of the end effector 240 may be increased by using materials exhibiting relatively high hardness and yield strength for the clevis 246 and head 260, such as the metals or metal alloys discussed above. As an example, the end effector 240, jaws 242, 244, actuation member 258, and clevis 246 may be configured according to the exemplary embodiments described in at least U.S. Patent App. Pub. No. US2014/0012290, entitled "REMOTELY ACTUATED SURGICAL GRIPPER WITH SEIZE RESISTANCE" and published on Jan. 9, 2014, and U.S. Patent App. Pub. No. US2014/0227106, entitled "SURGICAL INSTRUMENT DRIVE ELEMENT, AND RELATED DEVICES, SYSTEMS, AND METHODS" and published on Sep. 18, 2014, the entire contents of each of which is hereby incorporated by reference.

Also depicted in FIG. 4 are engagement features 264 of the distal portion 250 of the clevis 246 and engagement features 266 of the proximal portion 252 of the clevis 246.

As shown in FIG. 4, the engagement features 264 of the distal portion 250 and the engagement features 266 of the proximal portion 252 do not contact one another, but rather interlock with the intermediate portion 256 to form a robust and strong connection between the distal portion 250, the intermediate portion 256, and the proximal portion 252. Lack of contact between the electrically conductive distal portion 250 and proximal portion 252 and the separation of distal portion 250 and proximal portion 252 by the electrically insulating material of the intermediate portion 256 prevents electrical conduction between the distal portion 250 and the proximal portion 252. The distal portion 250 and proximal portion 252 may be characterized as being integrally connected with the intermediate portion 256. That is, the coupling between the distal portion 250 and the proximal portion 252 with the intermediate portion 256 may be considered an integral connection.

Figure 5:
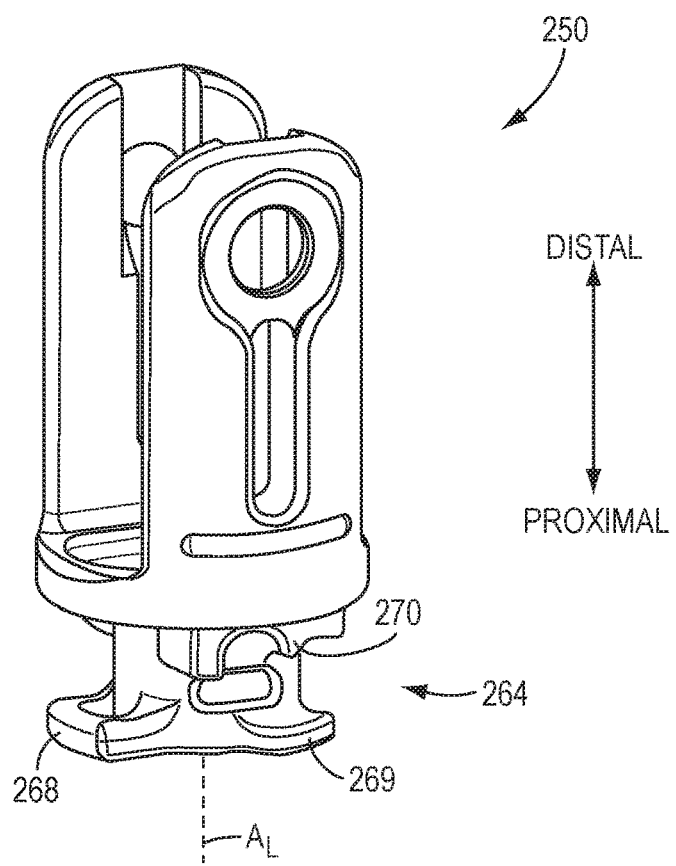
FIG. 5 is a perspective view distal portion of a clevis component of a surgical instrument according to an exemplary embodiment of the disclosure.

Referring now to FIG. 5, a detailed view of the distal portion 250 of the clevis 246 is shown in isolation to facilitate illustration of the engagement features 264. In the exemplary embodiment of FIG. 5, the engagement features 264 also include one or more flanges 268, 269 extending generally laterally (e.g., radially) with respect to a longitudinal axis $A_L$. Thus, flanges 268, 269 may also be termed lateral protrusions 268, 269. The engagement features 264 also include castellations 270 extending generally proximally along the direction of the longitudinal axis $A_L$. Castellations 270 may also be termed teeth or toothed structures.

Figure 6:
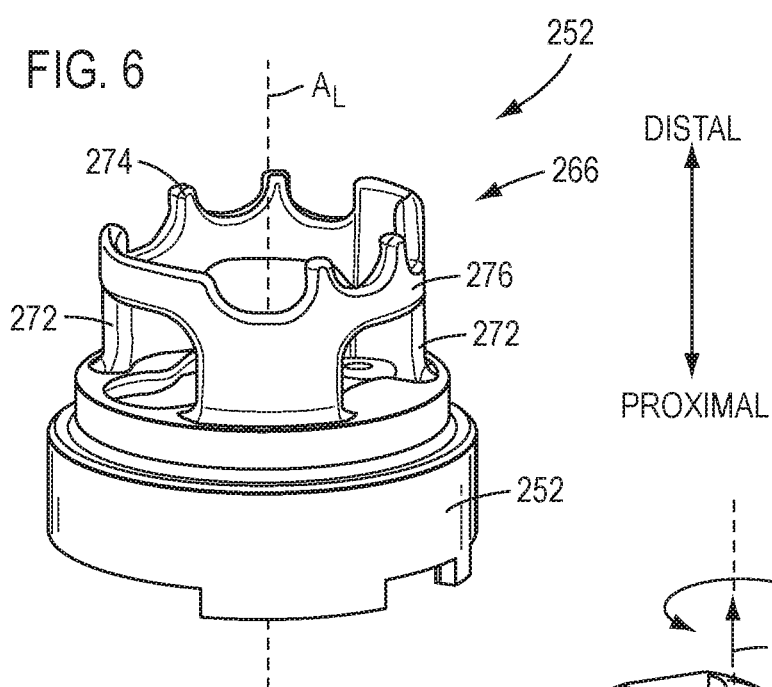
FIG. 6 is a perspective view of a proximal portion of a component of a surgical instrument according to an exemplary embodiment of the disclosure.
Figure 7:
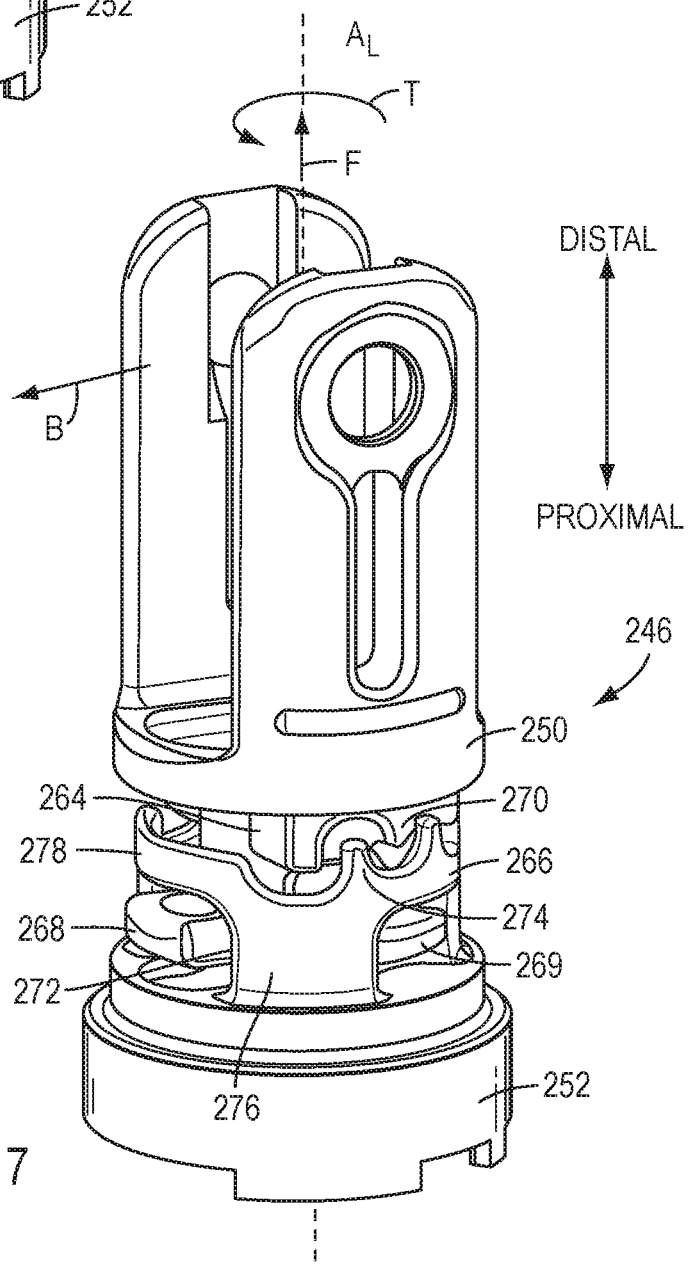
FIG. 7 is a perspective view of the distal portion of FIG. 5 and the proximal portion of FIG. 6 positioned together.

FIG. 6 is a detailed perspective view of the proximal portion 252 of the clevis 246 shown in isolation to facilitate illustration of the engagement features 266. In the exemplary embodiment of FIG. 6, the engagement features 266 are formed generally as an annular protrusion 276 extending distally from the proximal portion 252 along a longitudinal axis $A_L$. The annular protrusion 276 includes side openings 272 disposed about the circumference of the protrusion 276 and into which the flanges 268, 269 (FIG. 5) of the engagement features 264 of the distal portion 250 of the clevis 246 extend when the proximal portion 252 and distal portion 250 are positioned together, as shown in FIG. 7. The annular protrusion 276 also includes castellations (e.g., teeth or toothed structures) 274 extending from a distal end of the proximal portion 252. The castellations 274 are configured to be complementary to, although not in mating engagement with, castellations 270 shown in FIG. 5.

Referring now to FIG. 7, the distal portion 250 and the proximal portion 252 of the clevis 246 are shown together without the intermediate portion 256 (FIGS. 2 and 3) to illustrate the complementary nature of the engagement features 264 of the distal portion 250 and the engagement features 266 of the proximal portion 252. As shown in FIG. 7, the flanges 268 are positioned at least partially within the respective openings 272 of the distal portion 250 of the clevis 246. The castellations 270 of the distal portion 250 and the castellations 274 of the proximal portion 252 are partially meshed but not in contact with one another to avoid conduction of electrical current between the proximal portion 252 and the distal portion 250.

In some exemplary embodiments, the engagement features 264 of the distal portion 250 of the clevis 246 and the engagement features 266 of the proximal portion 252 of the clevis 246 may be configured such that tensile and compressive loads, bending loads, and torque loads placed on the clevis 246 create a compressive load on at least a portion of the intermediate portion 256 (FIGS. 2 and 3).

For example, with reference again to FIGS. 3 and 7, if the clevis 246 is subjected to a tensile load F along the longitudinal axis $A_L$, material of the intermediate portion 256 is placed in compression between the flanges 268 and a distal portion 278 of the annular protrusion 276. Similarly, if the clevis 246 is subjected to a bending load B, portions of the material of the intermediate portion 256 are placed under compressive loads. For example, if the clevis 246 is subjected to bending load B having a transverse component relative to the longitudinal axis $A_L$, the material of the intermediate portion 256 is placed in compression between a proximal surface of the lateral protrusion 268 and the proximal portion 252 of the clevis. At the same time, the material of the intermediate portion 256 also is placed in compression between a distal surface of the lateral protrusion 269 and the annular protrusion 276 of the proximal portion 252 of the clevis 246. If the bending load B is reversed in direction, then the material of the intermediate portion 256 is placed in compression between a distal surface of the lateral protrusion 268 and the annular protrusion 276 of the proximal portion 252, and the material of the intermediate portion 256 also is placed in compression between the proximal surface of the lateral protrusion 269 and the proximal portion 252. Similarly, if the clevis 246 is subjected to a torque T, then a portion of the material of the intermediate portion 256 is placed under a compressive load between the castellations 270 and 274, and between the flanges 268, 269 of the distal portion 250 and the annular protrusion 276 of the proximal portion within the openings 272.

Configuring the engagement features 264 and 266 of the distal portion 250 and proximal portion 252 of the clevis 246 such that portions of the material of the intermediate portion 256 are placed under compressive stress in response to various loads acting on the clevis enhances the strength of the clevis 246, for example, as compared to reliance on an adhesive bond strength between the intermediate portion 256 and the distal and proximal portions 250, 252. Because the intermediate portion 256 comprises a material dissimilar from the material of which the distal and proximal portion 250, 252 are comprised, some conventional methods of joining parts, such as welding, may not be possible. Thus, without the engagement features 264, 266, mechanical attachment between the distal portion 250 and the proximal portion 252 would rely on a material adhesion bond between the distal and proximal portions 250, 252 and the intermediate portion. However, by providing the engagement features 264, 266 that interlock with the intermediate portion 256 as discussed above, a strong, robust, and electrically insulating mechanical connection is formed between the distal portion 250 and the proximal portion 252.

In some exemplary embodiments, manufacture of the clevis 246 is accomplished as follows. The distal portion 250 and the proximal portion 252 are positioned so that the engagement features 264, 266 are in the relationship shown in FIG. 7. For example, the engagement features 264, 266 are positioned proximate one another, but separated by a void (e.g., air gap, etc.) with the lateral flanges 268 being at least partially received in the side wall openings 272. In an exemplary embodiment, the distal portion 250 and the proximal portion 252 are placed in a jig, mold, or other fixture in order to hold the portions 250, 252 in the appropriate spaced relationship. The intermediate portion 256 is then formed between the distal portion 250 and the proximal portion 252 by a process such as, for example, injection molding, casting, etc. Following molding of the intermediate portion 256, a seal member (such as seal member 786 (FIG. 8) or seal member 886 (FIG. 9) is molded over a portion of the proximal portion 252. The seal member 786, 886 may be formed of a polymer, such as, for example, silicone rubber, and may be molded using, for example, an injection molding process. Alternatively, in other exemplary embodiments, the seal member 786, 886 may be formed in a separate molding process (e.g., injection molding) and then inserted into the proximal portion 252. Other materials, such as other polymers, rubbers, etc., and other forming processes, such as other molding processes, additive manufacturing processes, etc. for forming the seal member 786 or 886 are within the scope of the disclosure. After the material of the intermediate portion 256 solidifies, the clevis 246 including the integrally connected distal portion 250, intermediate portion 256, and proximal portion 252 is removed from the mold or jig, and other components, such as the end effector 240 and instrument shaft 232 (FIG. 2), are assembled with the clevis 246.

Figure 8:
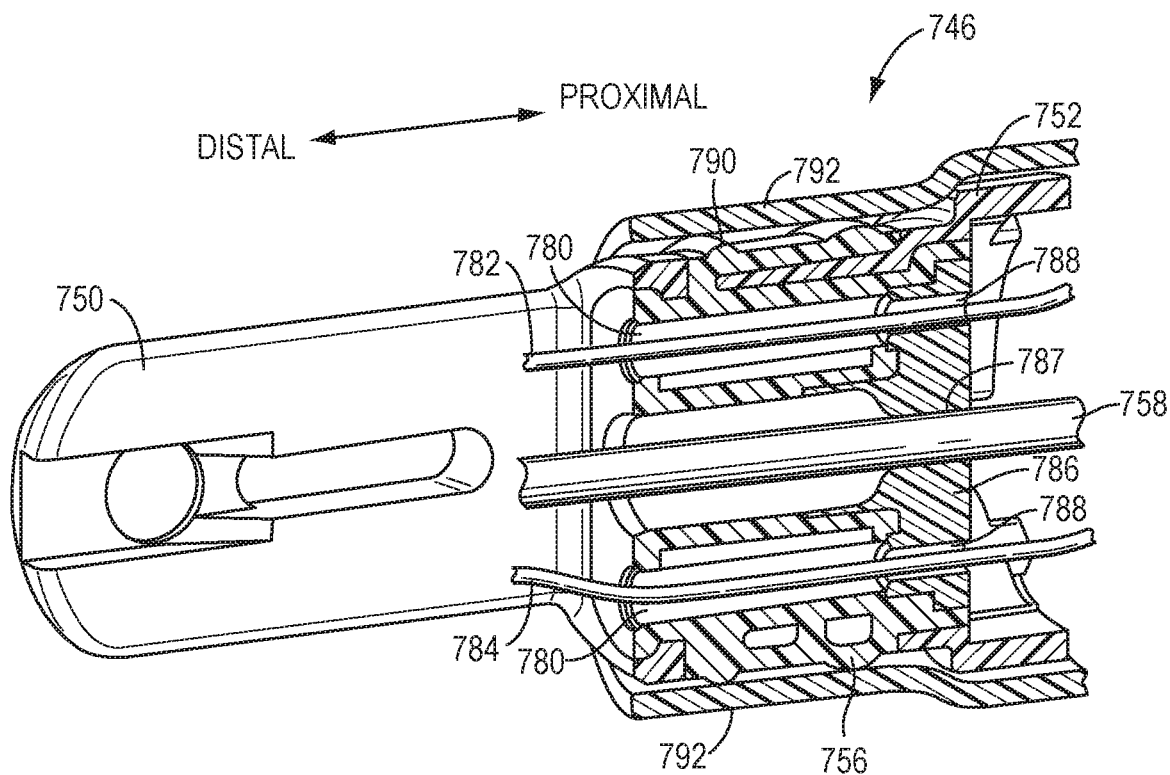
FIG. 8 is a partial, longitudinal cross-sectional view of a distal portion of a surgical instrument according to another exemplary embodiment of the disclosure.

Referring now to FIG. 8, a longitudinal cross-sectional perspective view of a clevis 746 according to an exemplary embodiment of the disclosure is shown. In the exemplary embodiment of FIG. 8, the clevis 746 includes a distal portion 750, a proximal portion 752, and an intermediate portion 756, as described above with respect to other exemplary embodiments. The intermediate portion 756 includes one or more passages 780 extending longitudinally between the proximal portion 752 and distal portion 750 of the clevis 746. In some exemplary embodiments, the one or more passages 780 may be used for routing flux conduits, such as electrical conductors 782, 784. In an exemplary embodiment, the electrical conductors 782, 784 conduct electrical current between an energy supply (not shown) of a surgical instrument (e.g., an energy supply associated with the patient side cart 100 shown in FIG. 1) and portions of an end effector (e.g., electrodes associated with jaws 242, 244 of end effector 240 (FIG. 3)).

Also shown in the exemplary embodiment of FIG. 8 is a seal member 786 positioned and configured to allow passage of, and to form a liquid seal with, an actuation member 758. In an exemplary embodiment, the seal member 786 comprises a relatively flexible, electrically insulating material, such as silicone rubber, to form a seal against the actuation member 258 to prevent liquid in and around a surgical site from forming a conductive path between the distal portion 750 and the proximal portion 752 of the clevis 746. When the end effector (e.g., end effector 240 shown in FIG. 3) is assembled, the actuation member 258 extends through a central passage 787 in the seal member 786. In an exemplary embodiment, the seal member 786 is molded over the distal portion 750 of the clevis 746 by, for example, an injection molding process, following molding of the intermediate portion 256 as noted above.

In the exemplary embodiment of FIG. 8, the seal member 786 includes passages 788 through which the electrical conductors 782, 784 pass. The electrical conductors 782, 784 are routed through the passages 780 and 788, and the material of the seal member 786 surrounding the passages 788 seals against an exterior surface of the electrical conductors 782, 784 (e.g., an electrically insulating jacket) to seal the passages 788 and prevent liquid from forming a conductive path between the distal portion 750 and the proximal portion 752 of the clevis 746.

Also illustrated in FIG. 8 are rounded annular ribs 790 protruding radially outward from the intermediate portion 756 of the clevis. The ribs 790 may interface with a portion 792 of a sheath (e.g., any of the sheaths disclosed U.S. Pat. No. 9,089,351 to Park et al., issued Jul. 28, 2015, entitled "Sheath for Surgical Instrument," or in U.S. Provisional Patent Application No. 62/276,471, filed Jan. 8, 2016, and titled "Sheaths for Surgical Instruments, and related Devices and Methods," the entire contents of each of which are incorporated by reference herein) disposed over the instrument shaft 232 (FIG. 2) to form a seal between the portion 792 of the sheath and the clevis 746. For example, the portion 792 of the sheath may comprise a relatively elastic, electrically insulating material that contacts the ribs 790 to form an external seal around the intermediate portion 756 of the clevis 746, thereby preventing liquids, tissue, or other biomaterial in the surgical site from forming a conductive path between the distal portion 750 and the proximal portion 752 of the clevis 746, for example, from external surface portions of the distal and proximal portions.

Figure 9:
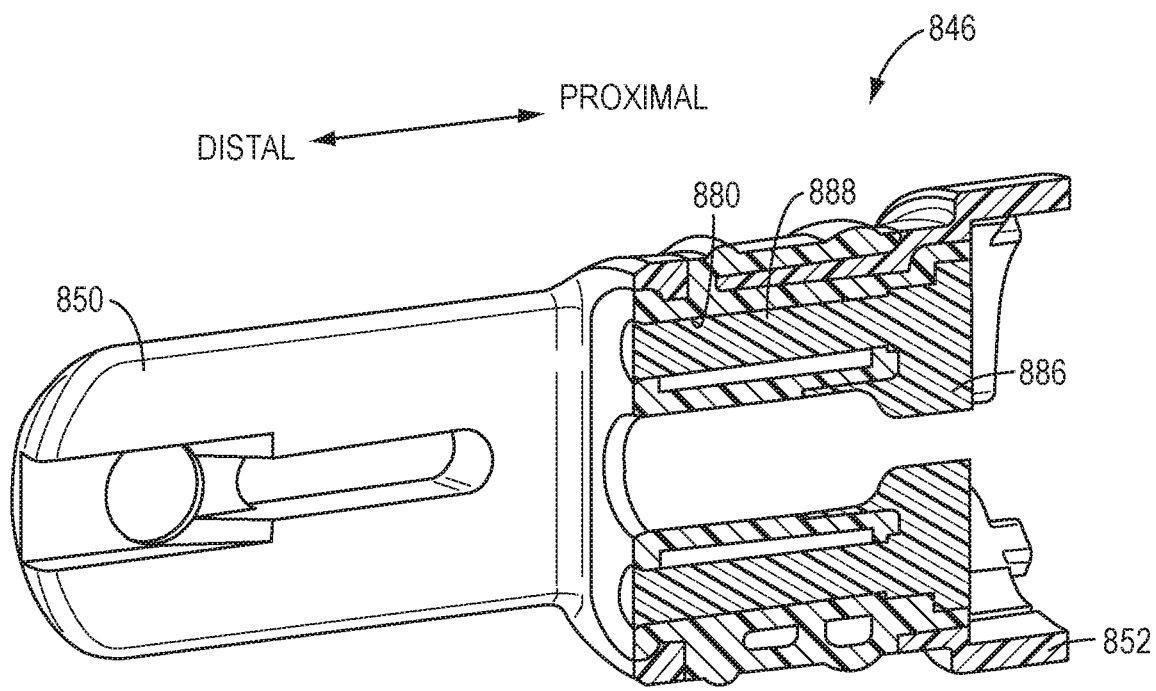
FIG. 9 is a partial, longitudinal cross-sectional view of a component of a surgical instrument according to yet another exemplary embodiment of the disclosure.

Referring now to FIG. 9, another exemplary embodiment of a clevis 846 is shown in longitudinal cross-section. In the embodiment of FIG. 9, the clevis 846 includes a seal member 886 configured for use with an end effector that is not coupled with flux conduits, such as electrical conductors 782, 784 (FIG. 8). In the embodiment of FIG. 9, the seal member 886 includes plugs 888 extending into and closing passages 880. The plugs 888 prevent liquids or other materials from forming a conductive path between the distal portion 850 and the proximal portion 852 of the clevis 846. Thus, similar tooling can be used to manufacture clevises 746 and 846, while different seal members 786 and 886 can be used to adapt similar clevises for use with end effectors that are used with or without flux conduits.

Surgical instrument components of various exemplary embodiments of the present disclosure provide electrical insulation between relatively distal and proximal portions of the instrument, while enabling the distal and proximal portions of the component to be made from high strength and durable materials, such as metals and/or metal alloys. Such construction thereby provides reliable operation and longevity due to the material characteristics of the metals/alloys, weldability of the component to other metal components of the surgical instrument, along with electrical insulation between the proximal and distal portions.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, although many of the embodiments described herein are in the context of surgery and surgical instruments, the techniques described can also be used with other medical procedures and instruments, and also for non-medical operations and instruments. As another example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the description and drawings and practice of the inventions disclosed herein. It is intended that the specification and embodiments disclosed be considered as exemplary only, with the claims being entitled to their full scope and breadth including equivalents.

What is claimed is:

1. A medical instrument component for coupling an end effector to a shaft of a medical instrument, the component comprising:
   an integral body comprising:
      a distal portion made of an electrically conductive first material and configured to couple to the end effector of the medical instrument;
      a proximal portion made of an electrically conductive second material and configured to couple to the shaft of the medical instrument; and
      an intermediate portion made of an electrically insulating third material, the intermediate portion being disposed between and integrally connecting the proximal portion and the distal portion, wherein the intermediate portion separates the distal portion and the proximal portion from contacting each other;
   wherein a cross-section of the medical instrument component taken transverse to a longitudinal axis of the medical instrument component contains at least a portion of the distal portion, at least a portion of the proximal portion, and at least a portion of the intermediate portion.

2. The medical instrument component of claim 1, wherein the first material and the second material each comprises a material selected from the group of materials consisting of metals and metal alloys.

3. The medical instrument component of claim 1, wherein the third material comprises a material selected from the group of materials consisting of: polymers, ceramics, and composites of polymers and ceramics.

4. The medical instrument component of claim 3, wherein the third material comprises polyphthalamide.

5. The medical instrument component of claim 1, wherein the intermediate portion is placed under a compressive load in response to the component being placed under any of a tensile load, a bending load, and a torque load.

6. The medical instrument component of claim 1, wherein the medical instrument component is a clevis.

7. The medical instrument component of claim 1, wherein the intermediate portion is integrally connected to the distal portion and to the proximal portion via interlocking engagement features.

8. The medical instrument of claim 7, wherein the interlocking engagement features comprise:
   at least one laterally outwardly extending flange formed in one of the distal portion and the proximal portion; and
   at least one opening formed in the other of the distal portion and the proximal portion, the at least one opening configured to accept at least a portion of the laterally outwardly extending flange.

9. The medical instrument component of claim 7, wherein the interlocking engagement features comprise engagement features with complementary teeth.

10. The medical instrument component of claim 1, further comprising:
   a central passage extending through the distal portion, through the intermediate portion, and through the proximal portion; and
   an electrically insulating seal member disposed in the central passage, wherein the seal member is configured to form a seal around an actuation member configured to pass through the central passage of the component.

11. A surgical instrument, comprising:
a shaft;
a clevis coupled to a distal end of the shaft, the clevis comprising an integral body comprising:
  a distal portion made of an electrically conductive first material;
  a proximal portion made of an electrically conductive second material and coupling the clevis to the shaft; and
  an intermediate portion made of an electrically insulating third material, the intermediate portion being disposed between and integrally connecting the proximal portion to the distal portion, wherein the intermediate portion separates the distal portion and the proximal portion from contact with each other;
  wherein a cross-section of the integral body taken transverse to a longitudinal axis of the integral body contains at least a portion of the distal portion, at least a portion of the proximal portion, and at least a portion of the intermediate portion; and
an end effector coupled to the distal portion of the clevis.

12. The surgical instrument of claim 11, wherein the surgical instrument comprises a bipolar instrument.

13. The surgical instrument of claim 11, wherein the end effector comprises:
one or more jaws coupled with the clevis, the surgical instrument further comprising:
an actuation member extending through a passage in the clevis and configured to actuate the one or more jaws.

14. The surgical instrument of claim 13, further comprising a seal member disposed in the passage of the clevis, the seal member configured to form a liquid seal around the actuation member.

15. The surgical instrument of claim 11, wherein the intermediate portion is molded in a space between the distal portion and the proximal portion of the clevis.

16. The surgical instrument of claim 11, wherein the intermediate portion comprises a material selected from the group of materials consisting of: polymers, ceramics, or composites of polymers and ceramics.

17. The surgical instrument of claim 16, wherein the intermediate portion comprises polyphthalamide.

18. A method of forming a component for coupling a surgical instrument end effector to a surgical instrument shaft, the method comprising:
arranging a first electrically conductive part distally and spaced from a second electrically conductive part; and
processing an electrically insulating material in the space to integrally connect the electrically insulating material to the first part and to the second part;
wherein after the integral connection;
the first part is a distal portion of the component, the second part is a proximal portion of the component, and the electrically insulating material is an intermediate portion of the component and separates the proximal portion and the distal portion from contact with one another, and
a cross-section of the component taken transverse to a longitudinal axis of the component contains at least a portion of the distal portion, at least a portion of the proximal portion, and at least a portion of the intermediate portion.

19. The method of claim 18, wherein processing the electrically insulating material in the space comprises flowing the electrically insulating material during an injection molding process.

20. The method of claim 18, wherein processing the electrically insulating material comprises casting.

21. The method of claim 18, wherein arranging the first electrically conductive part distally and spaced from the second electrically conductive part comprises arranging an engagement feature of the first part proximate a complementary engagement feature of the second part.

22. The method of claim 21, wherein arranging the engagement feature of the first part proximate the complementary engagement feature of the second part comprises arranging a laterally outwardly extending flange of the first part at least partially within an opening of the second part.

* * * * *